United States Patent
Benito et al.

(10) Patent No.: US 10,543,322 B2
(45) Date of Patent: Jan. 28, 2020

(54) INJECTION NEEDLE ASSEMBLY FOR AN INJECTION DEVICE AND AN INJECTION DEVICE COMPRISING SUCH ASSEMBLY

(71) Applicant: Novo Nordisk A/S, Bagsvaerd (DK)

(72) Inventors: Modesto Javier Mora Benito, Farum (DK); Soeren Kjellerup Hansen, Fjenneslev (DK); Helle Ravn Thomsen, Roedovre (DK); Daniel Patrick Godskesen True, Hellerup (DK)

(73) Assignee: Novo Nordisk A/S, Bagsvaerd (DK)

( * ) Notice: Subject to any disclaimer, the term of this patent is extended or adjusted under 35 U.S.C. 154(b) by 179 days.

(21) Appl. No.: 15/540,464

(22) PCT Filed: Jan. 22, 2016

(86) PCT No.: PCT/EP2016/051369
§ 371 (c)(1),
(2) Date: Jun. 28, 2017

(87) PCT Pub. No.: WO2016/116614
PCT Pub. Date: Jul. 28, 2016

(65) Prior Publication Data
US 2018/0001033 A1 Jan. 4, 2018

(30) Foreign Application Priority Data

Jan. 22, 2015 (EP) ...................................... 15152219
Dec. 30, 2015 (EP) ...................................... 15203134

(51) Int. Cl.
*A61M 5/32* (2006.01)
*A61M 5/20* (2006.01)
*A61M 5/24* (2006.01)

(52) U.S. Cl.
CPC ............ *A61M 5/3202* (2013.01); *A61M 5/20* (2013.01); *A61M 5/3204* (2013.01);
(Continued)

(58) Field of Classification Search
CPC .... A61M 5/3202; A61M 5/20; A61M 5/2033; A61M 5/3204; A61M 5/326;
(Continued)

(56) References Cited

U.S. PATENT DOCUMENTS 2,847,995 A 8/1958 Adams
3,734,080 A 5/1973 Petterson et al.
(Continued)

FOREIGN PATENT DOCUMENTS

AT 409456 B 8/2002
CN 202161323 U 3/2012
(Continued)

*Primary Examiner* — Nilay J Shah
(74) *Attorney, Agent, or Firm* — Wesley Nicolas

(57) ABSTRACT

An injection needle assembly (50) for an injection device, having a) a needle cannula (3) attached to a needle hub (4) and defining a pointed tip at a free end (3a, 3b), and b) a needle cover (10, 10a, 10b) forming an axially extending elongated flexible enclosure accommodating the needle cannula (3). The needle cover (10, 10a, 10b) is configured to axially collapse and become penetrated by the needle cannula (3) when a penetration force is applied to the needle cover. The needle cover (10, 10a, 10b) defines a shaft section (11a) and a bulb section (11b). The shaft section (11a) encircles the needle cannula (3) and extends axially from the needle hub (4) to the bulb section (11b). The shaft section (11a) comprises a collapsible wall area (15) having wall thickness $t_1$ less than a predefined wall thickness $t_{1,lim}$ to provide radial deformability for abutting contact with the needle cannula (3).

26 Claims, 9 Drawing Sheets

(52) U.S. Cl.
CPC .......... *A61M 5/326* (2013.01); *A61M 5/3286* (2013.01); *A61M 5/2033* (2013.01); *A61M 5/2466* (2013.01); *A61M 5/3243* (2013.01); *A61M 2005/206* (2013.01); *A61M 2005/247* (2013.01); *A61M 2005/2418* (2013.01); *A61M 2005/3247* (2013.01); *A61M 2005/3258* (2013.01); *A61M 2205/583* (2013.01)

(58) Field of Classification Search
CPC ...... A61M 5/2466; A61M 5/288; A61M 5/32; A61M 5/321; A61M 5/3243; A61M 2005/2013; A61M 2005/206; A61M 2005/3258; A61M 2005/247; A61M 2005/2474; A61M 2005/3246; A61M 2005/2418
See application file for complete search history.

(56) References Cited

U.S. PATENT DOCUMENTS

| | | | |
|---|---|---|---|
| 3,877,465 A | 4/1975 | Miyake | |
| 4,398,544 A | 8/1983 | Nugent et al. | |
| 4,775,369 A | 10/1988 | Schwartz | |
| 4,846,809 A | 7/1989 | Sims | |
| 4,986,818 A | 1/1991 | Imbert et al. | |
| 5,290,254 A * | 3/1994 | Vaillancourt | A61M 5/326 |
| | | | 128/919 |
| 5,540,664 A * | 7/1996 | Wyrick | A61M 5/002 |
| | | | 604/135 |
| 5,658,259 A * | 8/1997 | Pearson | A61M 5/2033 |
| | | | 604/136 |
| 6,110,160 A | 8/2000 | Farber | |
| 6,117,130 A * | 9/2000 | Kung | A61B 18/1492 |
| | | | 606/28 |
| 6,210,369 B1 | 4/2001 | Wilmot et al. | |
| 2004/0215107 A1 | 10/2004 | Sarstedt et al. | |
| 2008/0206936 A1* | 8/2008 | Fernandez-Ceballos | |
| | | | B82Y 10/00 |
| | | | 438/151 |
| 2011/0125100 A1 | 5/2011 | Schwirtz et al. | |
| 2012/0132209 A1* | 5/2012 | Rummery | A61M 16/06 |
| | | | 128/205.25 |
| 2013/0211330 A1 | 8/2013 | Pedersen et al. | |
| 2013/0317477 A1 | 11/2013 | Edwards et al. | |
| 2014/0261861 A1 | 9/2014 | Ivosevic et al. | |
| 2017/0361029 A1 | 12/2017 | Benito | |

FOREIGN PATENT DOCUMENTS

| | | |
|---|---|---|
| CN | 104162212 A | 11/2014 |
| DE | 3229783 C1 | 1/1984 |
| DE | 2004016791 U1 | 12/2004 |
| EP | 0409365 A1 | 1/1991 |
| WO | 9427660 A1 | 12/1994 |
| WO | 97/14455 A1 | 4/1997 |
| WO | 2009014955 A2 | 1/2009 |
| WO | 2012/022810 A2 | 2/2012 |
| WO | 2012025639 A1 | 3/2012 |
| WO | 2015123095 A1 | 8/2015 |

* cited by examiner

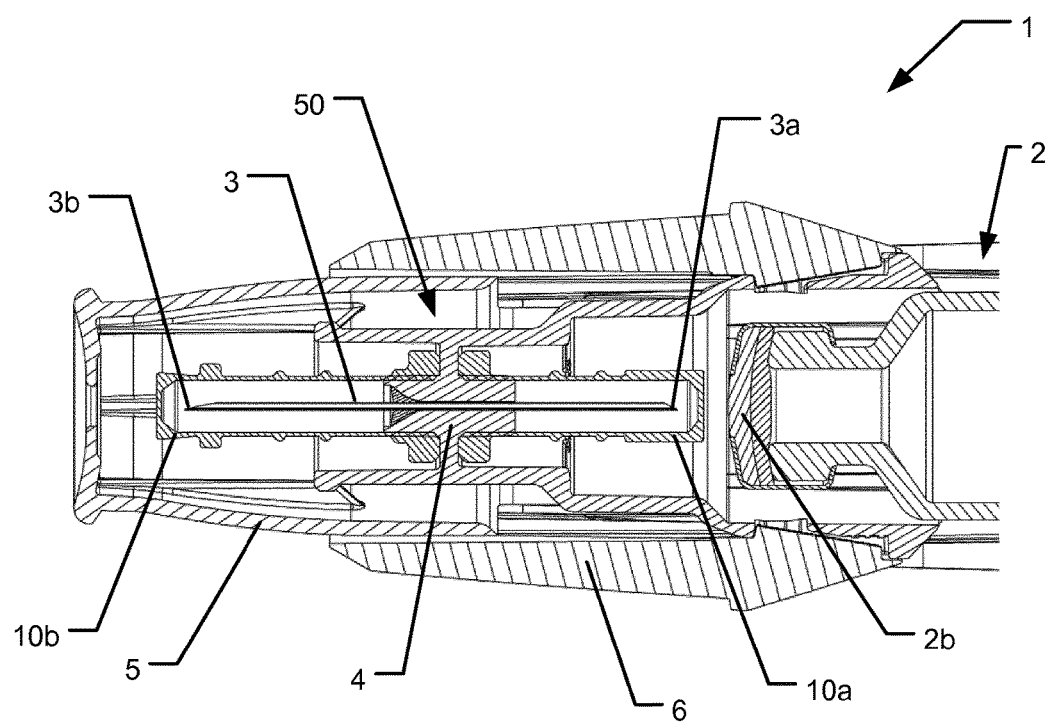
Fig. 7
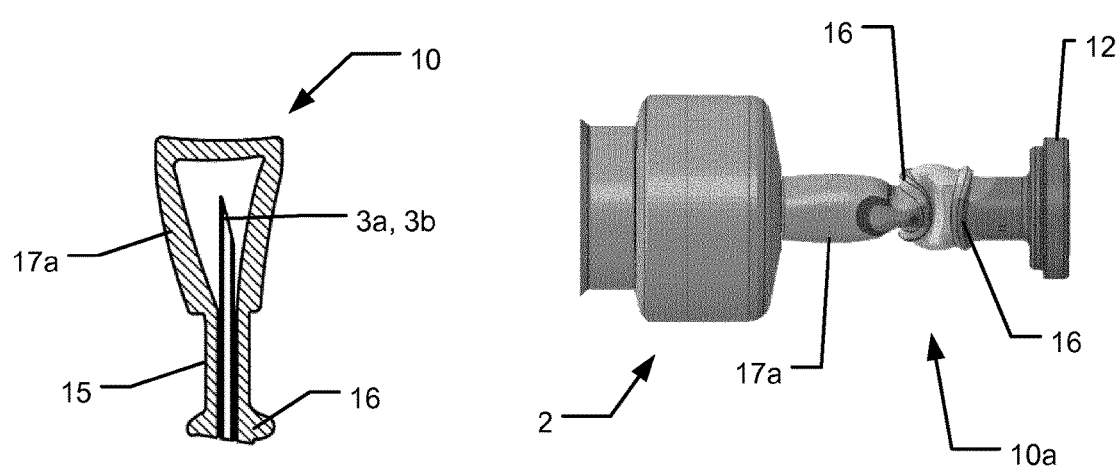
Fig. 6
Fig. 8

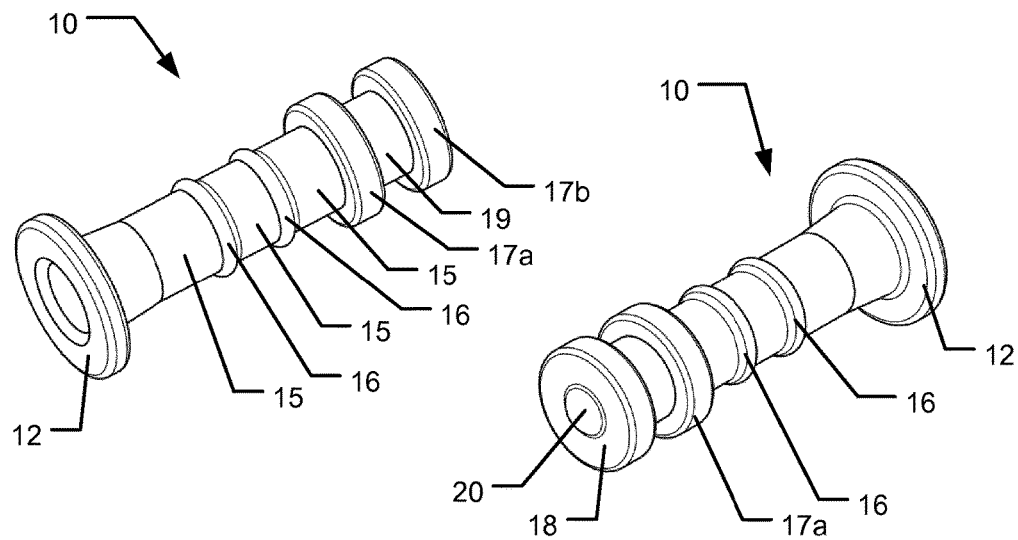
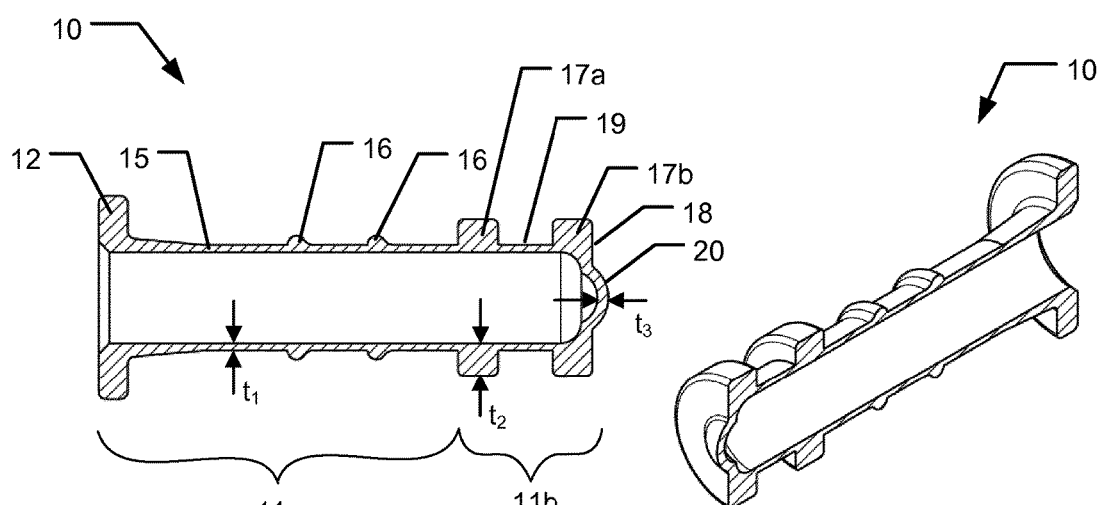

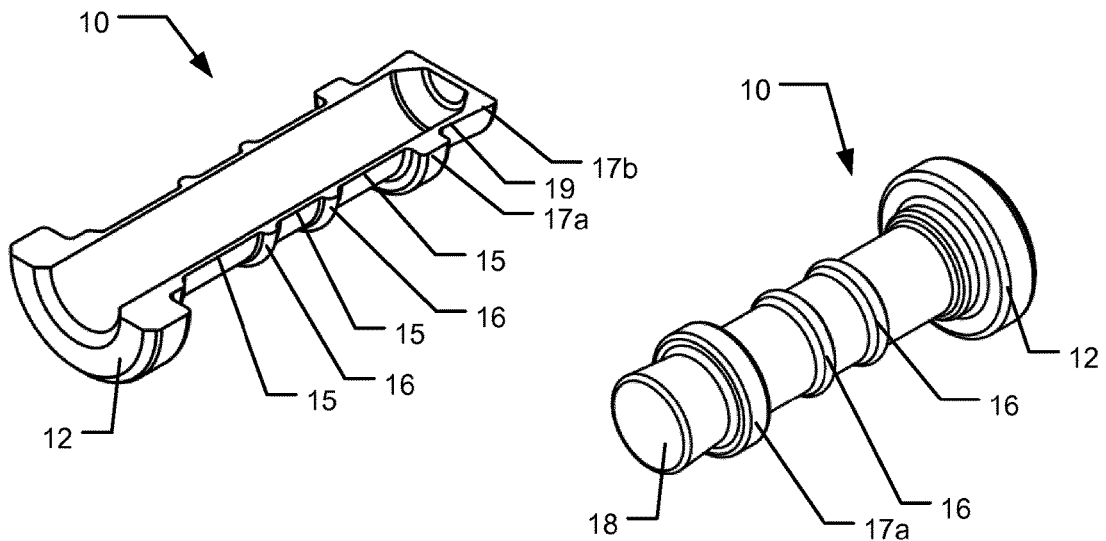
Fig. 10a
Fig. 10b
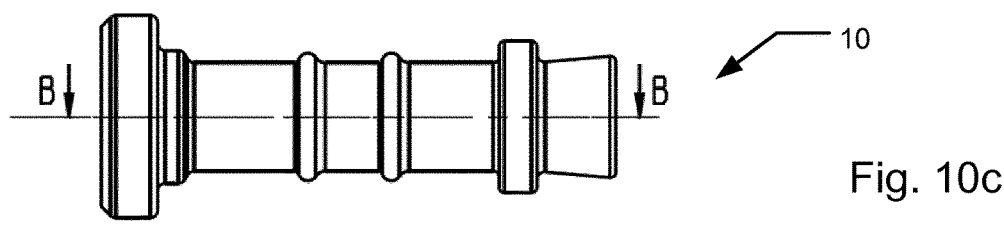
Fig. 10c
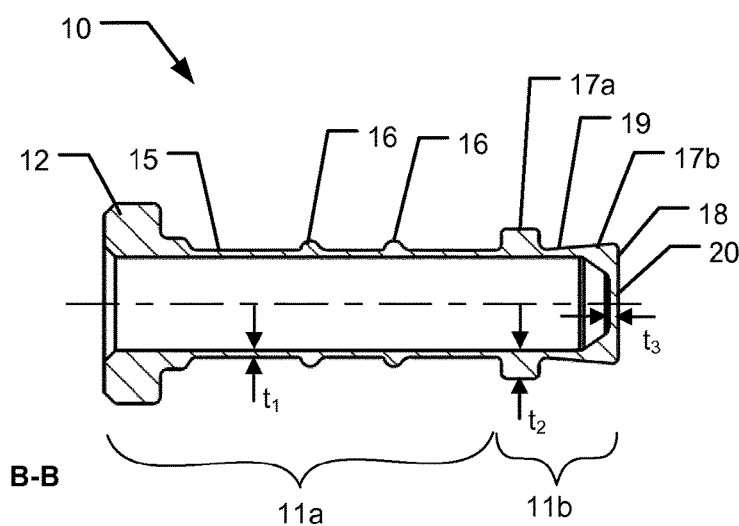
Fig. 10d

INJECTION NEEDLE ASSEMBLY FOR AN INJECTION DEVICE AND AN INJECTION DEVICE COMPRISING SUCH ASSEMBLY

CROSS-REFERENCE TO RELATED APPLICATIONS

This application is a 35 U.S.C. § 371 National Stage application of International Application PCT/EP2016/051369 (published as WO 2016/116614), filed Jan. 22, 2016, which claims priority to European Patent Application 15152219.0, filed Jan. 22, 2015, and priority to European Patent Application 15203134.0, filed Dec. 30, 2015; the contents of which are incorporated herein by reference.

FIELD OF THE INVENTION

The present invention relates to an injection needle assembly comprising a flexible needle cover and an injection device for injecting a medicament comprising such an injection needle assembly.

BACKGROUND OF THE INVENTION

Within development of medical devices it is of primary focus to develop devices that are safe. Yet it is also of particular concern that the medical devices are as simple and user-friendly as possible. Within medical injectors, such as auto-injectors, it is an aim that it involves no or little needle handling. Before use the needle must be kept sterile.

In some injection devices, the needle is protected by a needle cover, for example a resilient pierceable needle cover, which maintains a sterile barrier around the needle itself. Such needle cover is often assembled together with the needle to form a needle assembly.

By using a flexible pierceable needle cover as sterility barrier the needle can penetrate the sterility barrier thereby obviating the need for removing the needle cover prior to commencing the actual injection procedure. This eases the needle handling significantly. One example of an injector utilizing a pierceable front needle cover is disclosed in U.S. Pat. No. 5,658,259.

For medical injectors that utilize septum-based cartridges to expel one or more doses of a medicament the fluid pathway must be established by docking the injection needle relative to the cartridge. Still, this adds requirements to the sterile barrier system as it must be a safe and simple task to establish fluid communication. WO 2012/022810 discloses a medicament injector which incorporates a pair of flexible pierceable needle covers that prior to use maintains a front needle and a rear needle in a sterile state.

However, design and manufacture of needle assemblies that incorporate flexible pierceable needle covers often reveal issues of varying complexity. For example, if steam sterilization is used, pressure cycles used during the sterilization process may cause the injection needle to penetrate the needle cover thus compromising sterility of the final product. Further, requirements for enabling an effective and short sterilization within short product cycles often require use of needle covers of reduced wall thickness. However, reducing the wall thickness of needle covers will easily lead to further issues or disadvantages.

Further, a number of other factors have to be taken into account in designing needle covers that both provides for fault free operation and superior performance. For example, when utilizing thin injection needles in an injection device, as the device is actuated, the collapse and buckling of the needle cover may lead to non-axial and tilting collapsing of the needle cover which further may result in off-axis contact between the injection needle and the needle cover. Potentially, the injection needle may become bent which ultimately may cause a faulty device. Other important factors include considerations that relate to the force required for collapsing the needle cover as the device is operated such as during needle penetration or during device actuation. One aim is to obtain a low force for collapsing the needle cover.

Having regard to the above-identified prior art devices, it is an object of the present invention to provide a needle assembly and an injection device comprising a needle assembly that are improved with regards to safety in operation.

Yet additional further objects of the invention are to provide measures for obtaining needle assemblies and injection devices having a superior performance and, at the same time, enabling manufacture at a reduced cost.

BRIEF DESCRIPTION OF THE INVENTION

In a first aspect the present invention relates to an injection needle assembly for an injection device, the injection needle assembly comprising:
a needle cannula attached to a needle hub, the needle cannula extending along an axis from the needle hub towards a free end, and
a flexible needle cover forming an axially extending elongated enclosure accommodating the needle cannula, wherein the needle cover has a needle hub end mounted relative to the needle hub and a free end extending beyond the free end of the needle cannula, the needle cover being configured to axially collapse for being penetrated by the needle cannula when an axially directed penetration force is applied on the free end of the needle cover towards the needle hub, wherein the needle cover defines:
an elongated shaft section encircling the needle cannula and having a first axial end at the needle hub and a second axial end located axially between the needle hub and the free end of the needle cannula, the shaft section comprising a collapsible wall area that is radially deformable for abutting contact with the needle cannula, the collapsible area comprising an area having a wall thickness $t_1$ less than a predefined wall thickness $t_{1,lim}$ and
a bulb section connected to the second axial end of the shaft section and extending to a closed end surface at the free end of the needle cover, wherein the bulb section defines a bulb wall area axially overlapping and encircling the free end of the needle cannula wherein the bulb wall area comprises a wall area of wall thickness of at least $t_2$, wherein $t_2$ is greater than said range of predefined wall thicknesses and wherein the bulb section defines a central end wall area having a wall thickness $t_3$ smaller than the wall thickness $t_2$,
wherein the needle cover, in an initial non-penetrated state, assumes a first configuration wherein the wall areas of the bulb section and the wall areas of the shaft section are spaced apart from the needle cannula.

The axially extending elongated enclosure of the flexible needle cover, when attached to the needle hub, forms an enclosure that is contaminant-proof so that the needle cannula within the enclosure is guarded from contamination by the external environment.

The needle cover is formed of a resilient or flexible material adapted to allow penetration by the pointed tip of the needle cannula. The material of the needle cover is selected to substantially prevent microbes from passing through the needle cover but to allow a sterilant gas, such as steam, to pass through the needle cover. Non-limiting examples of suitable materials includes elastomeric materials include synthetic rubbers such as silicone rubbers, and organic rubbers, i.e. polyurethanes, polyacrylates and others; and natural rubbers such as latex. The injection needle assembly may be adapted for sterilization by steam sterilization.

The needle cover may be formed so that in the first configuration wherein the injection needle assembly is exerted to ambient air pressure and wherein no external forces act on the needle cover, no wall parts of the needle cover is in abutting contact with the needle cannula.

The free end of the needle cannula may be provided with a beveled portion that defines a pointed tip and a heel.

The bulb wall area of the bulb section having a wall thickness of at least $t_2$ may comprise an annular bulb region that axially overlaps the heel of the bevel when the needle cover assumes the first configuration.

When pressurized steam is utilized during sterilization of the injection needle assembly select portions of the shaft section of the needle cover is configured to radially collapse and contact the needle cannula at locations where the cannula does not exhibit any sharp geometry. In this way the shaft section may support the needle cannula while wall sections of the bulb section are maintained spaced apart from the sharp portions of the beveled tip end of the cannula. Hence, accidental penetration which potentially could compromise the sterility of the needle is prevented.

In exemplary embodiments the predefined wall thickness $t_{1,lim}$ is selected between 0.12 and 0.3 mm, preferably between 0.15 and 0.25 mm, and more preferably between 0.17 and 0.20 mm.

In exemplary embodiments, a major part of the wall areas of the shaft section, such as more than 50%, such as 60%, such as 70%, such as 80% comprise areas having wall thicknesses thinner than 0.3 mm.

An exemplary wall thickness for the central end wall area of the bulb section having a wall thickness $t_3$ may be selected between 0.20 to 0.35 mm, alternatively between 0.23 to 0.28 mm. The central end wall area of the bulb section may define a ventilation zone where the reduced wall thickness ensures effective steam penetration during steam sterilization. In addition the reduced wall thickness minimizes the risk of needle coring as the needle cannula pierces and penetrates through the central end wall area.

In some embodiments, when the needle cover assumes the first configuration, the second axial end of the shaft section is located between 0.2 to 2.0 mm from the heel, preferably between 0.4 to 0.8 mm from the heel. The said annular bulb region having a wall thickness of at least $t_2$ may extend axially from the second axial end of the shaft portion and axially overlap the heel of the bevel. In alternative embodiments, the annular bulb region having a wall thickness of at least $t_2$ may extend axially from the second axial end of the shaft portion all the way to the free end of the needle cover.

The wall area or the wall areas of the shaft section having a wall thickness $t_1$ less than predefined wall thickness $t_{1,lim}$ may be formed to directly connect to said annular bulb region.

In exemplary embodiments $t_2$ defines a wall thickness greater than 0.4 mm, preferably greater than 0.5 mm, more preferably greater than 0.6 mm and still more preferably greater than 0.7 mm. For some embodiments, for assembly reasons, a maximum of the wall thickness $t_2$ may be selected between 1 and 3 mm.

The bulb wall area may define first and second annular bulb regions that are axially spaced apart from each other by a set distance. In such embodiment, the first and the second annular bulb regions may comprise wall areas having a wall thickness of at least $t_2$. An annular region of reduced wall thickness between 0.15 to 0.35 mm, preferably between 0.18 to 0.25 mm may separate the first annular bulb region and second annular bulb region.

Said annular region of reduced wall thickness aids in providing a very low collapse force for the needle cover to be axially collapsed, i.e. when the free end of the needle cover is forced towards the hub for needle penetration. Such low collapse force is particularly beneficial in connection with auto-injectors that are triggered by needle shield movement. When an injection needle assembly as described herein is incorporated in such auto-injector a low trigger force can thus be enabled.

The said annular region of the bulb section having a reduced wall thickness may in certain embodiments be axially overlapping the pointed tip of the bevel.

The annular bulb regions may be formed by areas with a wall thickness $t_2$ that exhibit the same wall thickness throughout the circumferential and axial extension of the annular bulb regions. However, in other embodiments, the annular bulb regions may be formed with geometries that differ relative to each other. Each annular bulb region may be formed by areas with a uniform thickness or be defined by sub-areas of varying thickness.

In embodiments where said annular region of the bulb section has a reduced wall thickness that is axially overlapping the point of the bevel, to check for needle imperfections during assembly, the thin-walled section of the needle cover aids in enabling use of a vision arrangement for optical inspection of the point of the needle through a side wall section of the bulb section. The thin-walled section furthermore enables effective steam sterilization at the location of the needle tip.

In alternative embodiment the bulb section may comprise an annular region with a radially outwards facing surface that tapers into a larger diameter towards the free end of the needle cover and wherein a generally flat end surface is arranged at the extreme exterior end surface of the free end of the needle cover.

The end surface of the free end of the needle cover facing away from the needle cannula may be formed to generally mate with the surface of an element of an injection device that is configured for operating engagement with the needle cover.

When the cover serves as a front needle cover for covering a front needle, a flat end surface of the front needle cover may be configured for operating engagement with a flat surface of a coaxially arranged needle shield. As the needle shield is displaced axially towards the front needle cover, the flat surface of the needle shield engages the flat end surface of the front needle cover acting to support the front needle cover along the axis as the front needle cover is axially collapsed.

When the cover serves as a rear needle cover for covering a rear needle, a flat end surface of the rear needle cover may be configured for operating engagement with a septum area of a medicament cartridge that is axially aligned with but spaced apart from the needle cannula. As the medicament cartridge is displaced axially towards the rear needle cover, the septum area of the medicament cartridge engages the flat end surface of the rear needle cover acting to support the rear needle cover along the axis as the rear needle cover is axially collapsed.

Further means of improving visual or optical inspection may be facilitated. Subsequently to initially forming the needle cover at least a portion of the needle cover may be modified such as by pre-processing the needle cover to become spark eroded with a VDI less than 15 or preferably polished, more preferably with an A3 polishing. Such pre-processing ensures superior visibility of the needle cannula such as by inspection of the needle cannula at right angles to the axis of the needle cover. In exemplary embodiments, the entire needle cover is spark eroded or polished. Alternatively only areas located close to the pointed tip of the bevel are improved with respect to visual properties, enabling visual inspection of the needle tip such as by utilizing vision technology.

The needle cover may be provided so that, when it assumes the first configuration, it forms a radially inwards facing surface with a diameter within the range 1.5 to 4 mm, preferably within the range 2.2 to 3.0 mm, and more preferably between 2.4 to 2.6 mm. For assembly reasons, the inner geometry of the needle cover is formed so that it allows axially mounting of the needle cover relative to the needle hub without risking accidental penetration during the assembly stage. In some embodiments the radially inwards facing surface of the shaft section and/or the bulb section may exhibit a generally cylindrical shape. However, in other embodiments, the radially inwards facing surface may be of varying dimensions along its length and the cross sectional geometry may be other than circular.

The shaft section of the needle cover may in certain embodiments comprise one or a plurality of reinforcing ribs with increased wall thickness. For example, the reinforcing ribs may be formed with a wall thickness greater than 1.5 times $t_{1,lim}$, such as greater than 0.4 mm. The reinforcing ribs of the shaft section aids in ensuring a controlled axial collapse when a penetration force acts on the free end of the needle cover, the controlled axial collapse implying that the needle cover does not tend to tilt during axial collapse of the needle cover ensuring central penetration of the needle cannula through the central end wall area.

Example embodiments of the needle cover of the injection needle assembly includes a needle cover having a cylindrical inner surface with a diameter between 2.2 and 3.0 mm, wherein the annular collapse regions have a wall thickness between 0.15 and 0.25 mm, wherein the wall thickness at the reinforcing ribs have a thickness between 0.35 and 0.55 mm and wherein the bulb wall areas comprise areas having wall thicknesses between 0.4 and 0.9 mm.

In exemplary embodiments, such as when the needle cannula defines a front needle, the needle cannula of the injection needle assembly may be selected as one of a 28 gauge needle cannula, a 29 gauge needle cannula and a 30 gauge needle cannula. Further, exemplary needle lengths may include a needle cannula that extends between 6-10 mm from the needle hub.

A second aspect of the invention relates to an injection device comprising an injection needle assembly in accordance with said first aspect. Such injection device may further comprise a needle shield with a needle opening, the needle shield and the injection needle assembly being arranged axially slidably relative to each other for causing the needle cannula to penetrate the needle cover and protrude through the needle opening of the needle shield.

In certain embodiments the injection device is formed as an auto-injector that is triggerable by relative movement between the needle shield and the injection needle assembly. The auto-injector may be configured so that a front part of the needle is inserted manually into an injection site by holding the needle shield against an injection site and applying a manual force for moving the needle forward relative to the needle shield such as to cause the front needle to firstly penetrate the needle cover covering the front part of the needle and subsequently insert the front needle into the injection site.

The needle shield may thus be configured to act on the needle cover for causing the needle cover to be penetrated by the needle cannula. In particular embodiments, the needle shield, as it is being moved axially relative to the needle cover, engages the needle cover and thus forces the free end of the needle cover to move relative to the needle cannula which in turn leads to the needle cover being pierced and penetrated by the needle cannula.

In certain embodiments, the auto-injector is configured for being triggered upon the front needle reaching a pre-defined penetration depth. Such triggering may be facilitated by the user manually pushing the auto-injector against the injection site.

In certain embodiments the injection needle assembly is accommodated within the needle shield. The radially outwards facing surfaces of the shaft section and the bulb section of the needle cover may be radially spaced apart from the needle shield at least as the needle shield and the injection needle assembly slides relative to each other for causing the needle cannula to penetrate the needle cover. When forming the needle cover in accordance with the design features discussed within the present disclosure a particularly low collapse force required for collapsing and penetrating the needle cover by the front needle may be obtained.

The needle shield and the injection needle assembly according to this disclosure may form a sub-assembly wherein the injection needle assembly is accommodated within the needle shield and wherein the sub-assembly is suited for being subject to a sterilization process, such as steam sterilization.

In a third aspect the present invention relates to an injection needle assembly for an injection device, comprising:
  a needle hub,
  a needle cannula attached to the needle hub, the needle cannula being of elongated shape extending in a first direction along a needle axis from the needle hub towards a pointed tip, and
  a flexible needle cover forming an axially extending elongated enclosure accommodating at least a portion of the needle cannula, wherein the needle cover has a first end mounted relative to the needle hub and a second end extending beyond the pointed tip of the needle cannula, the needle cover being configured to axially collapse when a penetration force is applied on the second end of the needle cover towards the needle hub for penetrating the second end of the needle cover by the pointed tip of the needle cannula, wherein the needle cover defines:
  a shaft section encircling the needle cannula and extending along said needle axis away from the first end, the shaft section comprising wall areas of minimum wall thickness $t_1$, and
  a bulb section having bulb wall areas axially aligned with and encircling the pointed tip of the needle cannula and having a closed central end surface, the bulb section comprising wall areas having a wall thickness larger than said minimum wall thickness $t_1$, wherein the shaft section comprises one or more reinforcing ribs, each reinforcing rib extending non-parallel to the needle axis so as to at least partly encircle the needle cannula, wherein each reinforcing rib is disposed axially between the bulb section and the needle hub to divide adjoining collapse regions of the shaft section.

In this context the term "axially aligned with" means that two entities are arranged axially at the same location, such as when the two entities axially overlap each other.

According to the third aspect of the invention, the sterile barrier is safely maintained during sterilization since the geometry ensures the needle cannula will not penetrate the needle cover during the sterilization process. Also, it is ensured that suitable areas are provided for the sterilant gas or steam to penetrate the needle cover during sterilization. By designing the shaft section with one or more reinforcing ribs, a controlled collapse of the needle cover is obtained when an external force for penetrating the needle cover is applied to the needle cover.

The injection needle assembly may in a first variant define a needle cannula having only a single pointed end that is covered by a needle cover. Accordingly, the injection needle assembly may include an injection needle that is arranged for penetrating the skin at an injection site, i.e. defining a front needle, and wherein the needle cover forms a front needle cover. In other embodiments, the injection needle assembly may include an injection needle that is arranged for piercing a septum of a medicament cartridge, i.e. a rear needle, and wherein the needle cover forms a rear needle cover.

In second variants of the injection needle assembly according to the third aspect, said needle cannula extends from the needle hub in the first direction and defines a front needle, wherein said needle cover defines a front cover accommodating the front needle whereas the needle cannula further extends from the needle hub in a direction opposite to said first direction to a second pointed tip to define a rear needle and wherein the injection needle assembly further comprises a rear needle cover. In such needle assembly, said rear needle cover defines a flexible needle cover forming an axially extending elongated enclosure accommodating the rear needle, wherein the rear needle cover has a first end mounted relative to the needle hub and a second end extending beyond the pointed tip of the rear needle, the rear needle cover being configured to axially collapse when a penetration force is applied on the second end of the rear needle cover towards the needle hub for penetrating the second end of the rear needle cover by the pointed tip of the rear needle, wherein the rear needle cover defines:

a shaft section encircling the rear needle and extending along said needle axis away from the first end of the rear needle cover, the shaft section comprising wall areas of minimum wall thickness $t_1$, and a bulb section having bulb wall areas axially aligned with and encircling the pointed tip of the rear needle and having a closed central end surface, the bulb section comprising wall areas having a wall thickness larger than said minimum wall thickness $t_1$, wherein the shaft section comprises one or more reinforcing ribs, each reinforcing rib extending non-parallel to the needle axis so as to at least partly encircle the needle cannula, wherein each reinforcing rib is disposed axially between the bulb section and the needle hub to divide adjoining collapse regions of the shaft section.

In certain embodiments of the injection needle assembly, in a ready-to-use state, i.e. prior to application of said penetration force, the needle cover assumes a shape wherein all wall areas of the bulb section and the closed central end surface are spaced apart from the needle cannula. Also, in the same ready-to-use state, wall areas of the shaft section may be spaced apart from the needle cannula.

Said one or more reinforcing ribs may comprise ribs extending circumferentially at an angle of 90 degrees relative to the needle axis, wherein each reinforcing rib being arranged axially between two adjoining annular collapse regions.

In such design, when said penetration force is applied, opposing wall areas in the collapse regions are configured to radially deform on opposing sides of the needle cannula, such as deforming radially towards each other and deforming radially away from each other.

Opposing wall areas of each annular collapse region may be configured to radially deform when said penetration force is applied so that for each annular collapse region, two opposing wall areas deform radially towards each other and two opposing wall areas deform radially away from each other.

In certain embodiments, for a first annular collapse region, two opposing wall areas may be configured to deform radially towards each other along a first axis that extends normal to the needle axis and for an annular collapse region adjoining said first annular collapse region two opposing wall areas deform radially away from each other along said first axis.

In certain embodiments, at least one of said one or more reinforcing ribs extends 360 degrees circumferentially around the needle axis. In other embodiments, at least one of the reinforcing ribs extends more than 360 degrees around the needle axis and thus extends in a helical shape around the needle axis.

At least one of said one or more reinforcing ribs may be arranged to radially protrude from a radially outwards facing surface of the collapse region.

In some embodiments, said one or more reinforcing ribs comprise one or more reinforcing ribs disposed to extend in a helical shape around the shaft section.

In other embodiments, said one or more reinforcing ribs comprises a series of axially spaced apart part-circular rings disposed on alternating sides of the shaft section, such as semi-circular rings arranged 180 degrees apart along the length of the shaft section.

Wall areas of the shaft section may be formed exhibiting a cylindrical inner wall surface. In alternative embodiments, the shaft section may be formed so as to exhibit a conical wall surface, i.e. a frustoconical surface.

The wall thickness of wall areas of the shaft sectional locations of said one or more reinforcing ribs may be at least 1.2 times $t_1$, preferably at least 1.3 times $t_1$, more preferably at least 1.4 times $t_1$, and most preferably at least 1.5 times $t_1$.

The bulb wall areas may have a wall thickness of at least 1.5 times $t_1$, preferably at least 1.8 times $t_1$, more preferably at least 2.2 times $t_1$, and most preferably at least 2.5 times $t_1$.

In some embodiments the bulb section comprises at least one ventilation zone of reduced wall thickness surrounded by said bulb wall areas, said ventilation zone comprising wall areas having a wall thickness less than 2.5 times $t_1$, preferably less than 2.0 times $t_1$, and more preferably less than 1.5 times $t_1$.

The bulb wall areas may define first and second annular bulb regions, and wherein an annular region of reduced wall thickness being less than 2.5 times $t_1$, preferably less than 2.0 times $t_1$, and more preferably less than 1.5 times $t_1$ separates the first and second annular bulb regions. In other embodiments further annular regions of reduced wall thickness may be formed to axially divide the bulb section further.

The bulb section comprises a closed central end surface. The closed central end surface may comprise an area having a wall thickness less than 1.5 times $t_1$, preferably less than 1.3 times $t_1$, more preferably less than 1.2 times $t_1$, and most preferably less than 1.1 times $t_1$.

In some embodiments the closed central end surface of the bulb section defines a dome shaped surface where the dome shaped having a concave surface facing the pointed tip of the needle cannula.

In further embodiments, any combination of the features mentioned in accordance with the third aspect may additionally include features or variants mentioned in accordance with the first and second aspect of the invention.

In a fourth aspect the invention relates to a flexible needle cover as described herein to be included in an injection needle assembly or to be included in an injection device comprising an injection needle assembly as described above.

According to the current specification, the terms distal and proximal are used to describe the placement of the different elements with respect to each other. The term distal end should be understood as being the end which is closest to the skin of the user during injection while the term proximal end should be understood as the end which is farthest from the skin of the user during injection. In general, the user will hold the proximal end of the device while placing the distal end of the device on the skin during injection.

The term "minimum wall thickness" means that the collapse regions comprise at least one wall area having a specific wall thickness of $t_1$ and wherein other wall areas of the collapse regions may include areas of varying wall thickness such as wall areas of increased thickness compared to $t_1$. In some embodiments, the term "minimum wall thickness" means that the annular collapse regions comprise thin-walled areas having thicknesses being reduced compared to other areas of the needle cover so that at least one wall area of the annular collapse regions has a specific wall thickness of $t_1$ and wherein other wall areas of the annular collapse regions may include areas of varying wall thicknesses such as wall areas of increased thickness compared to $t_1$ and/or wall areas of decreased thickness compared to $t_1$.

It should be emphasized that the term "comprises/comprising/comprised of" when used in this specification is taken to specify the presence of stated features, integers, steps or components but does not preclude the presence or addition of one or more other features, integers, steps, components or groups thereof.

As used herein, the term "medicament" is meant to encompass any flowable drug capable of being passed through a delivery means such as a hollow needle or cannula in a controlled manner. Examples of flowable drugs are a liquid, a solution, a gel or a fine suspension. Also lyophilized drugs which prior to administration are dissolved into a liquid form are encompassed by the above definition. Representative medicaments includes for example pharmaceuticals, peptides, proteins (e.g. insulin, insulin analogues and C-peptide), hormones, biologically derived or active agents, hormonal and gene based agents, nutritional formulas and other substances in both solid (dispensed) or liquid form.

BRIEF DESCRIPTION OF THE DRAWINGS

In the following, the invention will be described in greater detail with reference to embodiments shown by the enclosed figures. It should be emphasized that the embodiments shown are used for example purposes only and should not be used to limit the scope of the invention.

FIG. 6 shows schematically a cross sectional side view of the tip portion of an injection needle and its needle cover during steam sterilization, FIG. 7 shows a cross sectional side view of the front portion of a first embodiment of an injection device incorporating a needle assembly according to the invention, FIG. 8 shows a side view of deformation of a rear needle cover as it cooperates with a distal part of a cartridge, FIGS. 9a-9d respectively show a perspective rear view, a perspective front view, a cross sectional side view and a perspective cross sectional view of a second embodiment of a needle cover in accordance with the present invention, FIGS. 10a-10d respectively show a perspective sectional rear view, a perspective front view, a side view and a cross sectional side view of a third embodiment of a needle cover in accordance with the present invention, FIGS. 11a-11d respectively show a perspective sectional rear view, a perspective front view, a side view and a cross sectional side view of a fourth embodiment of a needle cover in accordance with the present invention, FIGS. 12a-12d respectively show a perspective rear view, a perspective front view, a cross sectional side view and a perspective cross sectional view of a fifth embodiment of a needle cover in accordance with the present invention, and FIGS. 13a-13d respectively show a perspective rear view, a perspective front view, a cross sectional side view and a perspective cross sectional view of a sixth embodiment of a needle cover in accordance with the present invention.

DETAILED DESCRIPTION OF THE EMBODIMENTS

Figure 1:
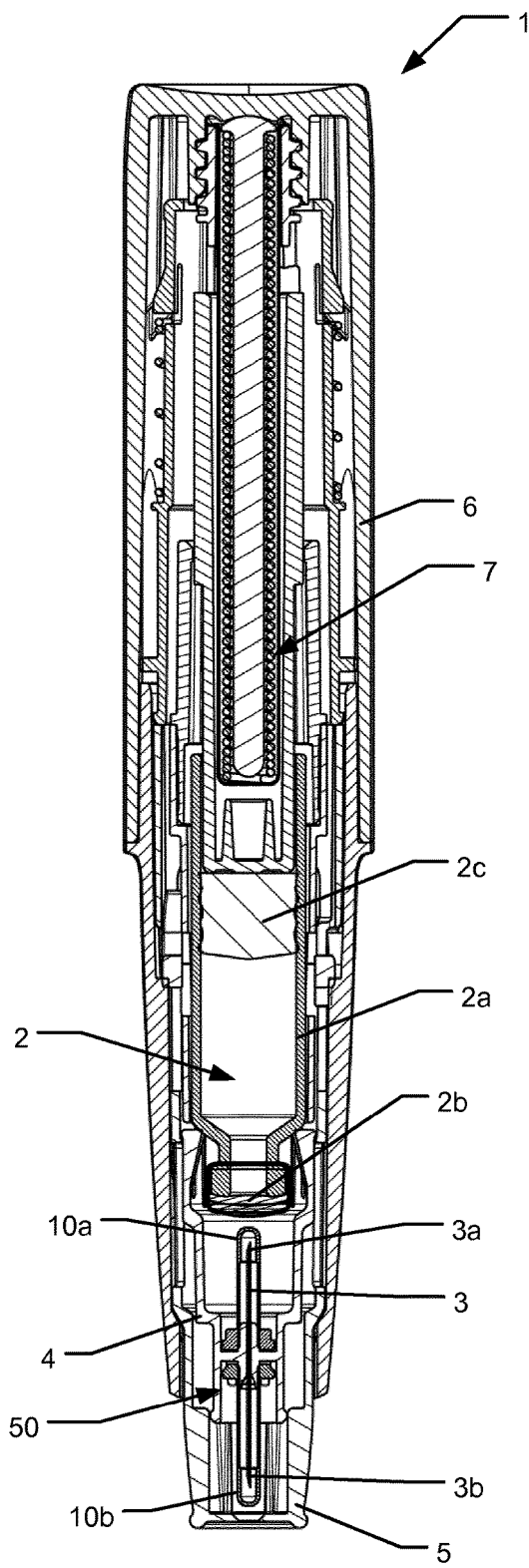
FIG. 1 shows a sectional side view of one example of an injection device suitable for incorporation of a needle assembly in accordance with the present invention, the needle assembly being in an initial shielded state.

FIGS. 1 to 4 illustrate operational states for an example injection device which incorporates a needle assembly in accordance with the present invention. The injection device is shown in four different states of operation in order to explain the basic function of the device.

It is to be noted that the shown injection device forms a non-limiting example and that the needle assembly of the present invention can be used together with other types of injection devices. All the details of the shown injection device will not be described in detail since these details have already been described in other patent specifications of the applicant. Reference is made to these other specifications for additional details.

FIGS. 1 to 4 show an injection device 1 with a medicament containing cartridge 2, an injection needle provided as a needle cannula 3 having a proximal end of the needle 3a and a distal end of the needle 3b, a needle hub 4, a needle shield 5, a housing 6 and an expelling assembly 7. The details of the expelling assembly will not be further described in this specification since the needle assembly of the present invention will work with many different types of expelling assemblies.

In the shown embodiment, in the shielded state as shown in FIG. 1, the distal end of the needle shield 5 is arranged distally to the distal end of the needle 3b. In this way, the needle is completely shielded by the needle shield. It can also be seen that in the current embodiment, the needle shield 5 is a single element which completely encases the needle assembly.

As can be seen from FIG. 1, the needle 3 is arranged as a needle cannula having two pointed ends, one arranged at the proximal end of the needle cannula and one arranged at the distal end. The needle hub 4 grips the middle portion of the needle cannula 3 so that both the distal and the proximal ends of the needle protrude axially relative to the hub 4, i.e. respectively forming a front needle and a rear needle. In the shown embodiment, the hub 4 is mounted fixedly relative to the housing 6. During use, the proximal end of the needle 3a is arranged to engage with a container 2 containing the medicament which is to be injected while the distal end of the needle 3b is arranged to pierce the skin of the user to inject the medicament into the body of the user.

In the shown embodiment, the container 2 forms a cartridge with a body 2a having a distally arranged outlet covered by a cartridge septum 2b adapted to be pierced by a needle for establishing fluid communication with the cartridge interior. The body of the cartridge accommodates a slidably arranged piston 2c. In the state where a needle has pierced cartridge septum 2b, piston 2c is drivable towards the outlet in order to dispense medicament from the cartridge 2. It should however be noted that the current invention could also be used in embodiments of an injection device where the needle assembly is arranged with only one pointed end having the needle connected to a source of medicament in another manner, without the use of a pierceable container septum as is shown in the appended figures.

As can also be seen from FIG. 1, the proximal end of the needle 3a is covered by a proximal needle cover 10a forming a flexible pierceable needle cover and the distal end of the needle 3b is covered by a distal needle cover 10b also forming a flexible pierceable needle cover. The needle covers 10a and 10b will also be referred to as a rear cover and front cover, respectively. Likewise, the part of the needle cannula that extends in a proximal direction from the hub will be referred to as the rear needle, whereas the part of the needle cannula extending in a distal direction from the hub will be referred to as the front needle. It is to be noted that in FIGS. 1 to 4 the shape of the needle covers 10a and 10b are only schematically depicted. The rear and front needle covers 10a and 10b are arranged to allow the needle to be sterilized and then ensure that the needle itself is not contaminated by further handling of the needle assembly.

Figure 2:
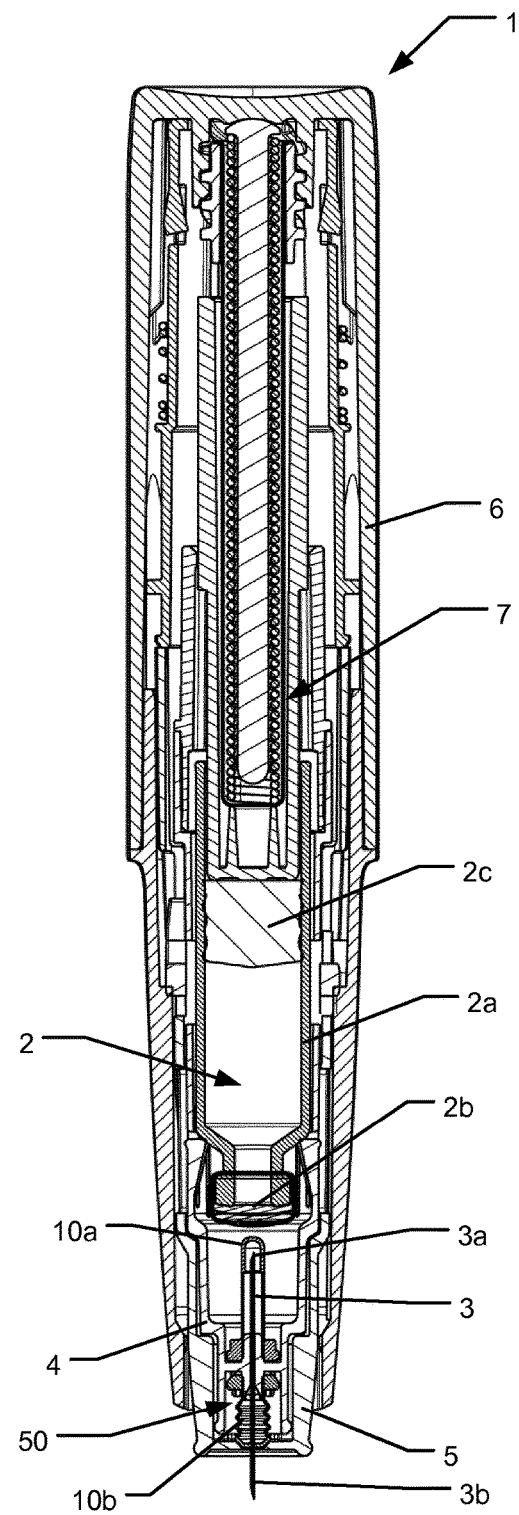
FIG. 2 shows a sectional side view of the injection device of FIG. 1 in a state where the distal end of the needle fully protrudes from a needle shield.

In FIG. 2, the needle shield 5 has been retracted with respect to the needle hub 4 such that the distal end of the needle 3b now extends distally past the distal end 5b of the needle shield. In this way the distal end of the needle 3b is now exposed and ready for fluid communication with a user. As can also be seen in FIG. 2, the act of retracting the needle shield has caused the distal needle cover 10b to be pulled back. This causes the distal end of the needle to pierce through the needle cover thereby uncovering the distal end of the needle. Due to the flexible nature of the needle cover, the needle cover is easily retracted.

Figure 3:
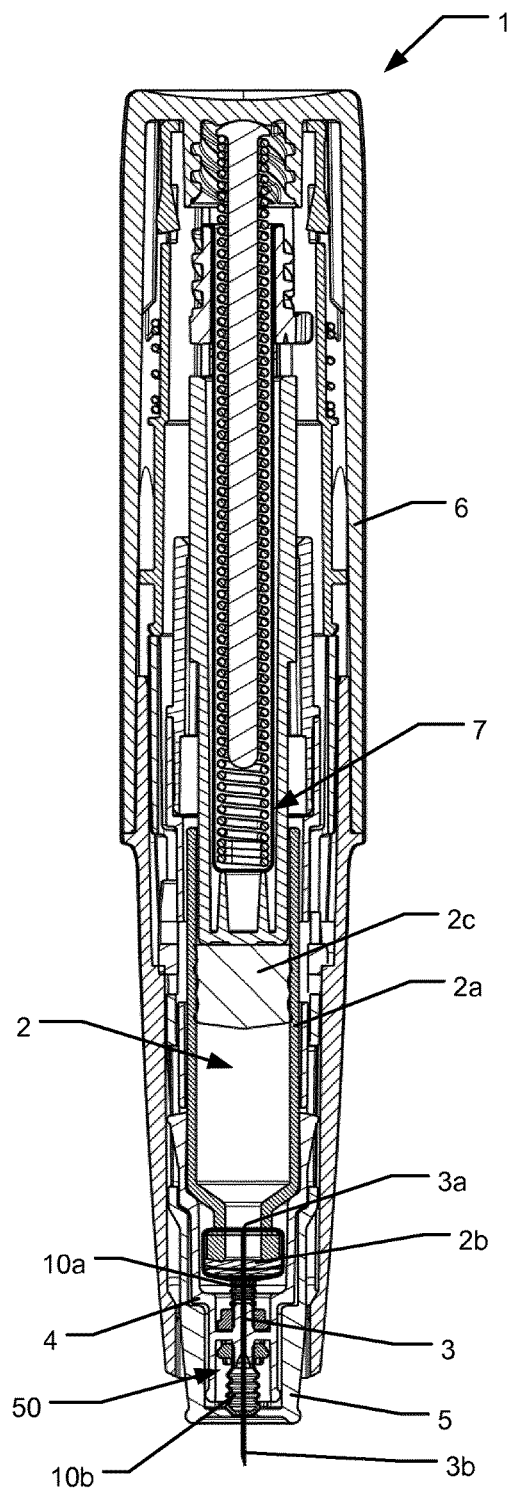
FIG. 3 shows a sectional side view of the injection device of FIG. 1 in a state where a cartridge has been connected to the proximal end of the needle for fluid delivery and wherein expelling has been initiated.

In the shown embodiment, the act of retracting the needle shield relative to the needle hub activates the expelling assembly which initially provides a force for moving the cartridge 2 relative to the housing 6. In FIG. 3, it can be seen that the expelling assembly 7 has pushed the medicament containing cartridge 2 forward in a distal direction to engage the cartridge with the proximal end of the needle. The proximal end of the needle punctures the septum of the cartridge thereby establishing a fluid path from the cartridge through the needle and to the distal end of the needle whereby the medicament can be injected into the user at the selected injection site. As can also be seen in FIG. 3, the proximal needle cover 10a has also been compressed by the motion of the cartridge towards the needle. This thereby uncovers the proximal end of the needle and allows it to engage with the cartridge.

Figure 4:
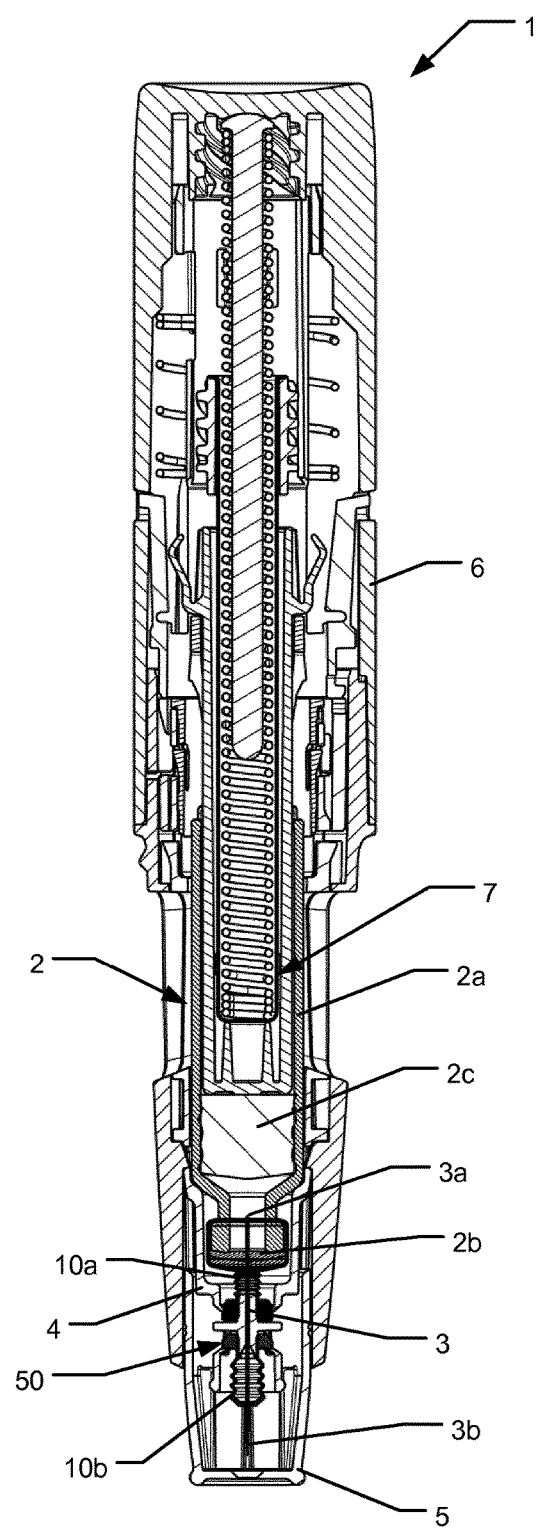
FIG. 4 shows a sectional side view of the injection device of FIG. 1 in a state where the needle shield has returned to its original position to put the needle into a shielded state again, FIGS. 5a-5d respectively show a perspective rear view, a perspective front view, a cross sectional side view and a perspective cross sectional view of a first embodiment of a needle cover in accordance with the present invention.

In FIG. 4, the expelling assembly has pushed the piston 2c arranged in the cartridge downwards, thereby causing the medicament in the cartridge to be injected through the needle into the injection site. After the medicament has been injected, the needle shield is again pushed forward with respect to the needle hub to shield the distal end of the needle. In the shown embodiment, this occurs as a consequence of the user manually retracting the housing 6 of the injection device relative to the injection site. In the shown embodiment, the needle shield 5 is biased in the distal direction by means of a needle shield spring.

The description above with respect to FIGS. 1 to 4 has been provided to give a background of the use of an injection device. The injection device described is one of many different available injection devices. It should be noted that the needle assembly of the current invention can be used with different injection devices, not just the one described above with respect to FIGS. 1 to 4. During manufacture of the injection device, the needle assembly will be subjected to a sterilization procedure so that it is ensured that the needle assembly is in a sterile condition.

FIGS. 5 to 13 show different views of a needle assembly 50 and, in particular, a variety of needle covers for use in such needle assemblies in accordance with the current invention. The needle assembly according to the invention may in different variants include a front needle only, variants including a rear needle only or variants including both a front needle and a rear needle. Flexible needle covers may be arranged to encase respective needle ends.

FIGS. 5a, 5b, 5c and 5d respectively show a perspective rear view, a perspective front view, a cross sectional side view and a perspective cross sectional view of a first embodiment of a needle cover 10 which may be used for sealing either the front needle or the rear needle of a particular needle assembly. The needle cover 10 is formed as an axially extending elongated enclosure formed for accommodating the part of the needle cannula 3 that extends axially from the first end, i.e. the needle hub 4 end. In the shown embodiment, the interior wall surface has a generally cylindrical shape that is closed off at its free end opposite the needle hub end by a closed central end surface 18. The needle cover is made from a flexible pierceable material. In the shown embodiment, the needle cover is made from a liquid silicon rubber having shore A 70.

Figure 5A:
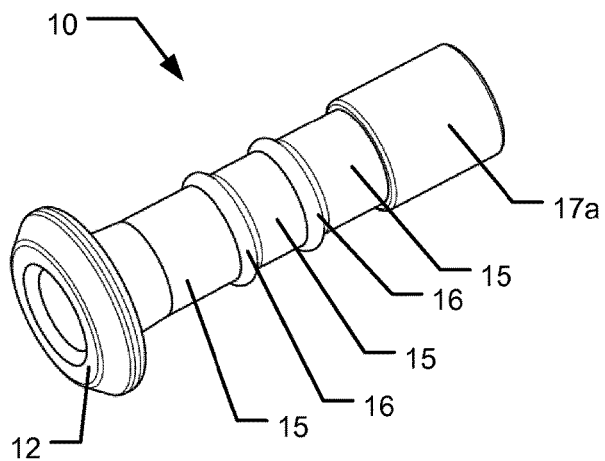
Figure 5B:
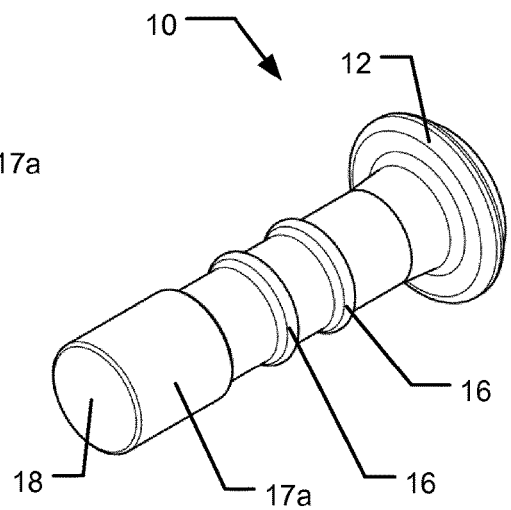
Figure 5C:
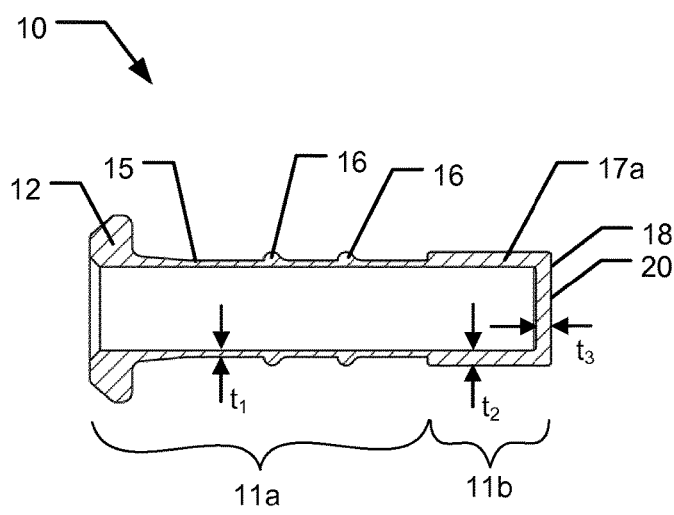
Figure 5D:
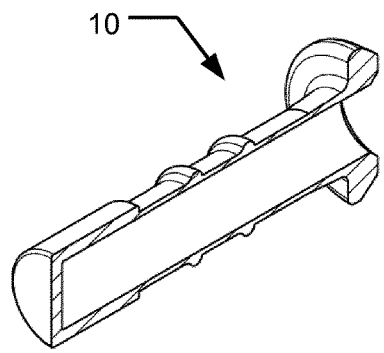
Figure 11A:
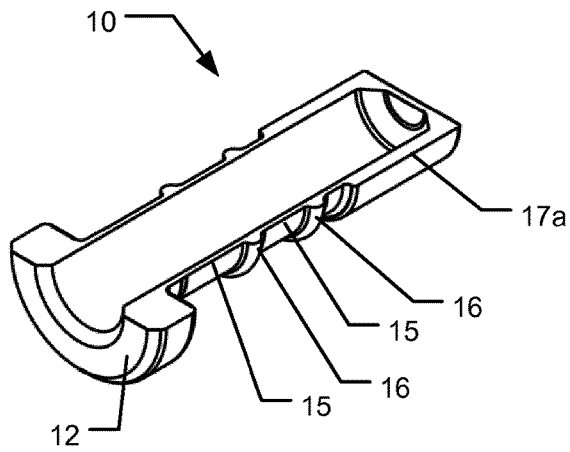
Figure 11B:
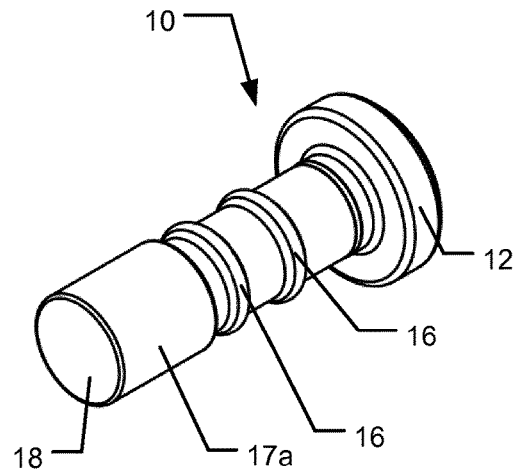
Figure 11C:
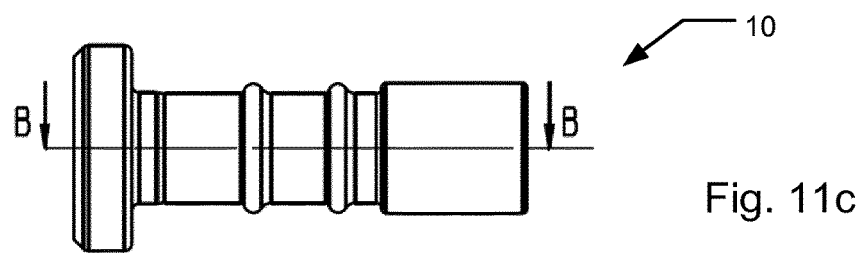
Figure 11D:
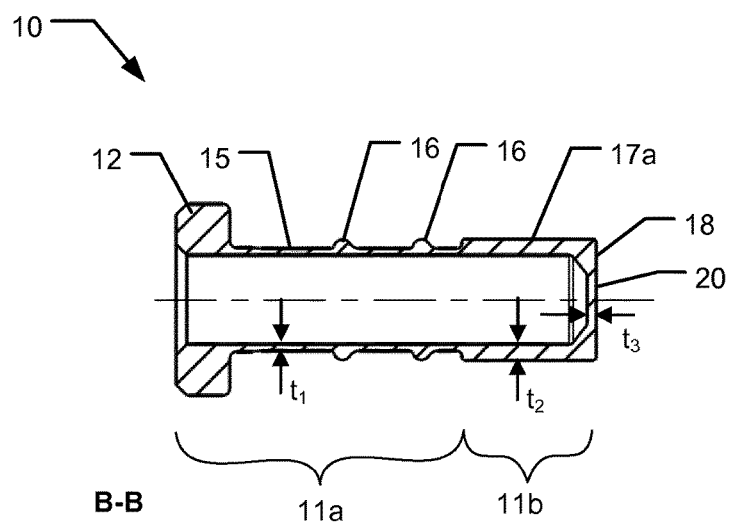
Figure 12A:
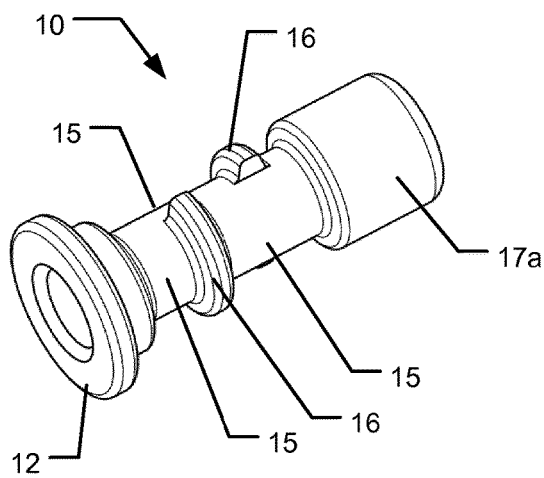
Figure 12B:
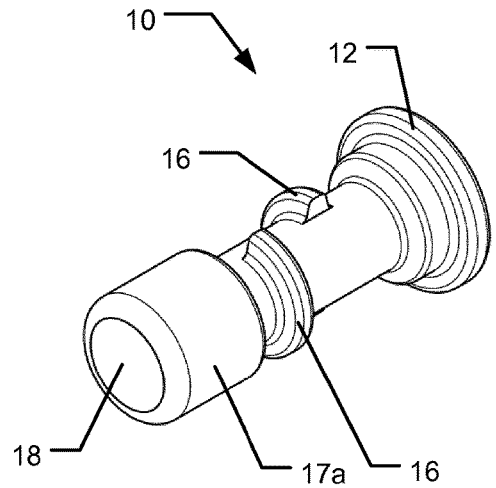
Figure 12C:
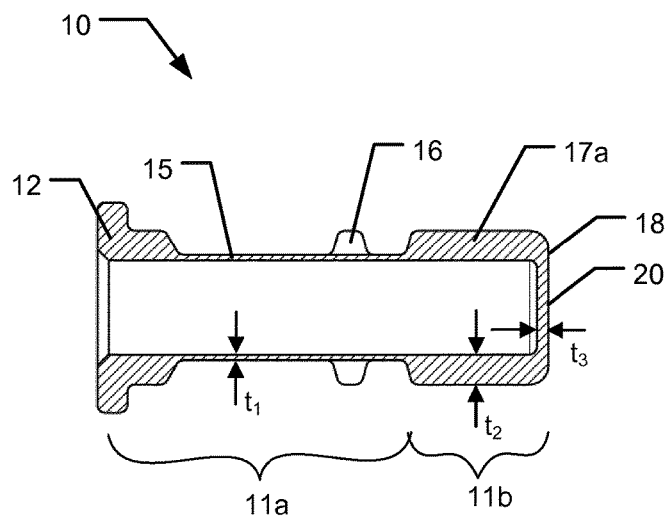
Figure 12D:
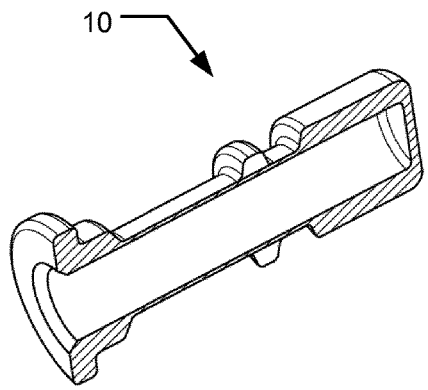
Figure 13A:
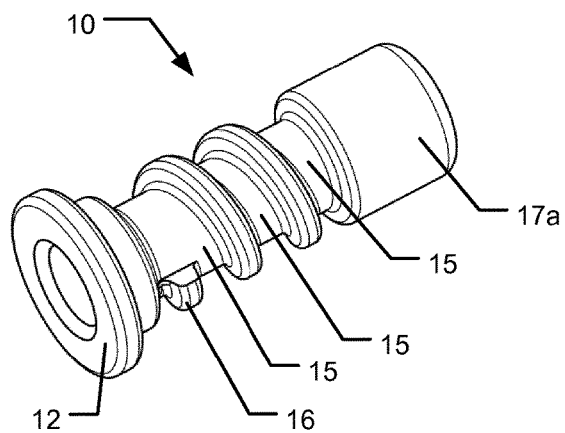
Figure 13B:
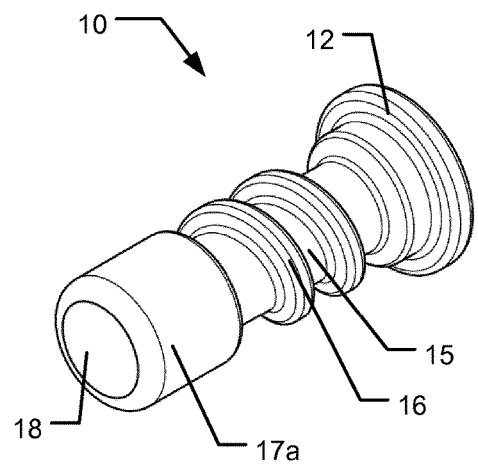
Figure 13C:
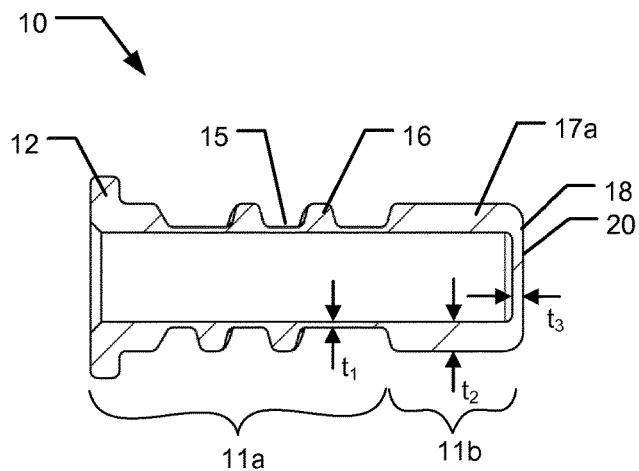
Figure 13D:
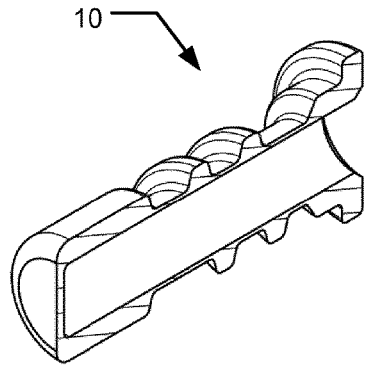

Referring mainly to FIG. 5c, the needle cover 10 is basically formed by two sections, i.e. a shaft section 11a that mounts to the needle hub, and a bulb section 11b that connects to the shaft section at a location axially opposite to the needle hub. The bulb section is formed so as to encircle the free end of the needle cannula and for closing off the end of the needle cover 10.

The shaft section 11a is formed as a generally thin-walled cylindrical object having a rim portion 12 that is configured for mating and mounting relative to the needle hub 4. A number of circular reinforcing ribs may be formed on the exterior surface of the shaft section 11a. Each reinforcing rib encircles the needle cannula at a particular axial location between the bulb section and the needle hub and thus divides two annular regions that may be referred to as collapse regions 15 of the shaft section 11a. In the shown embodiment, two ribs 16 are distributed along the length of the shaft section. However, other embodiments may include less or more reinforcing ribs 16 distributed along the length of the shaft section 11a, such as one, three, four or five. In other embodiments, the shaft section does not include reinforcing ribs.

In the shown embodiment, the bulb section 11b is formed as a cylinder with bulb wall areas 17a having a wall thickness $t_2$ larger than the wall thickness $t_1$ of the collapse regions 15. The bulb section 11b extends from the free end of the needle cover 10 to the shaft section 11a so that the bulb section 11b axially overlaps the pointed tip of the needle by a particular margin. The end wall located at the free end of the needle cover may exhibit a wall thickness with a wall thickness $t_3$ smaller than the wall thickness $t_2$ of bulb wall areas 17a.

With reference to FIG. 6, which schematically shows a part of the needle assembly 50 during steam sterilization, the varying pressure during pressure cycles of a steam sterilization process tend to sequentially radially collapse and expand the shaft section 11a. At some instances, the thin-walled areas of the needle cover deforms and collapses first and makes the thicker material in the tip form a protective "bulb" around the needle tip. The increased wall thickness of the bulb wall areas 17a effectively stiffens the bulb section 11b meaning that the bulb section is able to withstand the pressure so that no parts of the bulb section 11b gets into contact with the sharpened parts of the needle cannula. Hence, the risk that the needle cover 10 unintentionally becomes pierced by the needle cannula 3 during steam sterilization will be effectively lowered.

With reference to FIG. 7, which shows a detailed view of the distal portion of a second embodiment of an injection device 1, the needle assembly 50 comprises a needle hub 4, a proximal end of the needle 3a, a distal end of the needle 3b, a rear needle cover 10a and a front needle cover 10b. FIG. 7 further depicts a distal portion of the needle shield 5, a distal portion of the housing 6 and a distal portion of the cartridge 2. Each of the rear needle cover 10a and front needle cover 10b may be formed generally as shown in FIGS. 5a-5d. As seen in FIG. 7, respective ones of the needle covers 10a and 10b is mounted relative to the hub 4 so as to snugly fit a cylindrical mounting surface formed on the needle hub. Non-limiting examples for fixation of the needle cover relative to the needle hub may include a press-fit or include further mechanical fastening elements that squeezes and withhold the rim portion 12 of the needle cover, such as by means of a snap action. It is seen that, for the shown embodiment, the needle covers are formed so that when no external forces act to deform the needle covers the internal wall surfaces of the needle covers are spaced apart from their respective parts of the needle cannula without touching it. However, during operation of the device 1, as described in connection with FIGS. 1-4, the relative movement between the needle shield 5 and the housing 6, and subsequently the relative movement between the cartridge 2 and the needle cannula 3, the needle covers 10b and 10a will become axially compressed and ultimately penetrated by the pointed tips of the respective parts of the needle cannula 3.

FIG. 8 depicts a simulation of deformation of the rear needle cover 10a as it cooperates with the distal part of the cartridge 2 at a particular point in time during operation of the device, i.e. during relative axial movement between the cartridge 2 and the proximal end of the needle 3a. Initially, the needle cover 10a is spaced apart from the septum 2b of the cartridge 2. However, during relative axial movement, the closed central end surface 18 of bulb section 11b of the rear needle cover 10a will abut the distal part of cartridge 2. The rear needle cover 10a, in particular the shaft section 11a, will initially start to deform. Due to the reinforcing ribs 16, a controlled deformation will mainly start at the collapse regions 15. Pairs of opposing wall areas in the collapse regions 15 on opposite sides of the needle cannula 3 will either start to deform radially towards each other or radially away from each other. The reinforcing ribs 16 however ensure that the shaft section 11a will not start to tilt with respect to the needle axis. As a consequence, a controlled axial collapse is ensured and the potential risk that the pointed needle tip should penetrate the closed central end surface 18 at a location offset from the intended one is minimized. This means that the risk that the proximal end of the needle 3a will become bent during collapsing of the needle cover will be minimized.

For the shown embodiment of the rear needle cover 10a, for a first annular collapse region 15, two opposing wall areas deform radially towards each other along a first axis that extends normal to the needle axis. Further deformation of the needle cover 10a means that for annular collapse regions 15 adjoining said first annular collapse region two opposing wall areas deform radially away from each other along said first axis.

The same considerations apply for the front needle cover 10b where reinforcing ribs 16 may be disposed to ensure that the distal end of the needle 3b will not be unintentionally bent during movement of the needle shield 5 relative to the distal end of the needle 3b.

As a further means for ensuring a controlled axial collapse of the needle covers 10a and 10b, the shape of the central end surfaces 18, respectively adapted to abut the distal face of the cartridge 2 and the proximal surface of the needle shield 5, may be formed in agreement with the shape of these abutting elements. The abutting surfaces of the central end surface 18 may for example be formed as a substantial flat surface, such as being formed as a circular planar surface.

The wall thickness of the "thin walled areas" of the needle cover 10, such as the collapse regions 15, is selected to allow steam to penetrate the material in a rate suitable for steam sterilization. In the shown embodiments, a wall thickness $t_1$ of thin walled areas may be selected in the order of 0.18 mm. As non-limiting examples, in the first embodiment, the collapse regions 15 may be formed with a wall thickness in the range of 0.15-0.22 mm, the reinforcing ribs 16 may have a wall thickness in the range of 0.22-0.25 mm, whereas the wall areas 17 of the bulb section 11b may be selected with a wall thickness in the range of 0.40-0.80 mm. The radially inwards facing surface of needle cover may be formed with an internal diameter about 2.5 mm to provide for safe assembly of the needle cover relative to the cannula. Non-limiting exemplary needle cannulas for the distal end of the needle 3b may be selected as a 28 gauge needle having a length between 6-10 mm. Depending on the particular application, the rear needle may typically be selected with an increased lumen to facilitate greater flow velocities.

FIGS. 9a to 9d show a second embodiment of a needle cover 10 in views corresponding to the views shown in FIGS. 5a to 5d. In the second embodiment, the bulb section 11b has mainly been modified relative to the first embodiment, by introducing an annular band 19 of reduced wall thickness axially dividing relatively thick walled first and second annular bands of bulb wall areas 17a and 17b. In the shown embodiment, the annular bands of bulb wall areas 17a and 17b are formed by areas with a wall thickness $t_2$ that exhibit the same wall thickness throughout the circumferential and axial extension of annular bands bulb wall areas 17a and 17b. However, in other embodiments, the annular bands of bulb wall areas 17a and 17b may be formed with geometries that differ relative to each other. Each annular band of bulb wall areas 17a and 17b may be formed by areas with a uniform thickness or be defined by sub-areas of varying thickness. The annular band 19 serves to lower the compression force needed when axially deforming the needle cover 10 during operation of the injection device. The bulb section 11b however still effectively aids in minimizing the risk of unintentional piercing of the bulb section 11b during steam sterilization. Further, a ventilation zone 20 located at the central end surface 18 may be introduced with a reduced wall thickness $t_3$. The annular band 19 and the ventilation zone 20 aid in flow of steam towards the interior of the bulb section 11b during steam sterilization. As indicated in FIG. 6, the radial collapsing of the shaft section 11a of the needle cover 10 may tend to introduce a gasket effect lowering flow of steam towards the tip section of the needle cannula. The ventilation zone and the annular band 19 thus aid in providing steam towards the tip of the needle cannula as well as to the interior lumen of the needle cannula. Further, the reduced thickness of ventilation zone 20 reduces the risk of needle coring as the needle pierces and penetrates through the central end surface 18. The ventilation zone 20 may be formed as a flat surface. However, other shaped surfaces, such as a dome-shaped surface may be selected for the ventilation zone 20.

FIGS. 10a to 10d show a third embodiment of a needle cover 10 in different views. Compared to the second embodiment, the bulb section 11b has been changed so that the annular band 19 of reduced thickness and the second annular band of bulb wall area 17b having a thick wall have been replaced by a tapered section that increases in diameter towards the free end of the needle cover 10. The first annular band of bulb wall area 17a of wall thickness $t_2$ still divides the bulb section 11a from the shaft section 11b. The bulb section 11b still exhibits an annular region 19 with reduced wall thickness whereas the inner circumferential edge at the free end of the needle cover performs as a strengthening zone in the second annular band of bulb wall area 17b to provide the necessary rigidity to prevent the bulb from collapsing during steam sterilization. A central end wall area 20 performs as a ventilation zone having a wall thickness ($t_3$) smaller than wall thickness ($t_2$), such as between 0.20 and 0.3 mm, such as between 0.23 and 0.28 mm.

FIGS. 11a to 11d show a fourth embodiment of a needle cover 10 in different views. This embodiment most closely resembles the first embodiment. The differing features mainly involve a central end wall area 20 with reduced wall thickness performing as a ventilation zone and ensuring reduced risk of coring during penetration of the needle cannula 3 through wall area 20. Again, at the free end of the needle cover, the inner circumferential edge is provided with stiffening geometries.

FIGS. 12a to 12d show a fifth embodiment of a needle cover 10 in views corresponding to the views shown in FIGS. 5a-5d. In the fifth embodiment, the shaft section 11a has mainly been modified relative to the first embodiment in that the circular reinforcing ribs 16 of the first embodiment have been replaced by semi-circular bands 16 that alternatingly have been arranged on either side of the shaft section 11a. Again, the reinforcing ribs 16 divide the remaining parts of the shaft section 11a into collapse regions 15. The action of each reinforcing rib 16 serves to ensure a controlled axial collapse of the shaft section upon application of a penetration force. The reinforcing ribs 16 define predetermined locations where the needle cover 10 will start deformation allowing further ribs 16 to control the progression of the axial collapse. In the shown embodiment, two semi-circular ribs 16 have been shown but in other embodiments a different number of semi-circular ribs may be selected. Also, ribs having a different angular extension than 180 degrees extension can be used.

FIGS. 13a-13d show a sixth embodiment of a needle cover 10 in views corresponding to the views shown in FIGS. 5a-5d. In the sixth embodiment, the shaft section 11a has been modified relative to the first embodiment in that the circular reinforcing ribs 16 of the first embodiment have been replaced by helical rib 16 that extends around the shaft section 11a in a helical fashion. The thin-walled areas located between segments of the helical rib 16 form collapse regions 15.

It is to be noted that the figures and the above description have shown and described the example embodiments without describing each individual feature shown in the drawings. Furthermore, many of the details have not been described in detail since the person skilled in the art should be familiar with these details and they would just unnecessarily complicate this description.

Furthermore, some preferred embodiments have been shown in the foregoing, but it should be stressed that the invention is not limited to these, but may be embodied in other ways within the subject matter defined in the following claims and within the remaining disclosure.

The invention claimed is:

1. An injection needle assembly for an injection device, comprising:
   a needle cannula attached to a needle hub, the needle cannula extending along an axis from the needle hub towards a free end of the needle cannula, and
   a flexible needle cover forming an axially extending elongated enclosure accommodating the needle cannula, wherein the needle cover has a needle hub end mounted relative to the needle hub and a free end extending beyond the free end of the needle cannula, the needle cover being configured to axially collapse for being penetrated by the needle cannula when an axially directed penetration force is applied on the free end of the needle cover towards the needle hub, the needle cover defining:
   an elongated shaft section encircling the needle cannula and having a first axial end at the needle hub and a second axial end located axially between the needle hub and the free end of the needle cannula, the shaft section comprising a collapsible wall area that is radially deformable for abutting contact with the needle cannula, the collapsible wall area comprising an area having wall thickness $t_1$ less than a predefined wall thickness $t_{1,lim}$, and
   a bulb section connected to the second axial end of the shaft section and extending to a closed end surface at the free end of the needle cover, wherein the bulb section defines a bulb wall area axially overlapping and encircling the free end of the needle cannula wherein the bulb wall area comprises wall areas having wall thicknesses of at least $t_2$, wherein the $t_2$ is greater than said predefined wall thickness $t_{1,lim}$, and wherein the bulb section defines a central end wall area having a wall thickness $t_3$ smaller than the wall thickness $t_2$, wherein the needle cover, in an initial non-penetrated state, assumes a first configuration wherein the bulb wall area, the central end wall area and the collapsible wall area of the shaft section are spaced apart from the needle cannula, wherein the bulb wall area [17a, 19, 17b] defines a first annular bulb region [17a] and a second annular bulb region [17b], the first and second bulb regions [17a, 17b] comprising the wall areas having wall thicknesses of at least $t_2$, and wherein an annular region [19] of reduced the wall thickness between 0.15 mm to 0.35 mm separates the first annular bulb region [17a] and the second annular bulb region [17b], and wherein the central end wall area of the bulb section has the wall thickness $t_3$ selected between 0.20 mm to 0.35 mm.

2. The injection needle assembly as defined in claim 1, wherein the free end of the needle cannula is provided with a beveled portion that defines a pointed tip and a heel and wherein said bulb wall area of the bulb section having the wall thickness of at least $t_2$ comprises at least one of the first or second annular bulb region that axially overlaps the heel of the beveled portion when the needle cover assumes the first configuration.

3. The injection needle assembly as defined in claim 2, wherein, when the needle cover assumes the first configuration, the second axial end of the shaft section is located between 0.2 mm to 2.0 mm from the heel and wherein said at least one of the first or second annular bulb region having the wall thickness of at least $t_2$ extends axially from the second axial end of the shaft section and axially overlaps the heel of the bevel.

4. The injection needle assembly as defined in claim 2, wherein the wall area of the shaft section having the wall thickness $t_1$ less than the predefined wall thickness $t_{1,lim}$ connects to said at least one of the first or second annular bulb region.

5. The injection needle assembly as defined in claim 2, wherein, when the needle cover assumes the first configuration, the second axial end of the shaft section is located between 0.4 to 0.8 mm from the heel and wherein at least one of the first or second annular bulb region having the wall thickness of at least $t_2$ extends axially from the second axial end of the shaft section and axially overlaps the heel of the beveled portion.

6. The injection needle assembly as defined in claim 1, wherein the $t_2$ defines the wall thickness greater than 0.4 mm.

7. The injection needle assembly as defined in claim 1, wherein said annular region of the bulb section having reduced wall thickness is axially overlapping a pointed tip of a beveled portion.

8. The injection needle assembly as defined in claim 1, wherein the bulb section comprises at least one of the first or second annular bulb region with a radially outwards facing surface that tapers into a larger diameter towards the free end of the needle cover and wherein a generally flat end surface is arranged at an extreme exterior end surface of the free end of the needle cover.

9. The injection needle assembly as defined in claim 1, wherein at least a portion of said needle cover is spark eroded with a VDI less than 15.

10. The injection needle assembly as defined in claim 1, wherein the needle cover, in the first configuration, comprises a radially inwards facing surface with a diameter within the range 1.5 mm to 4 mm.

11. The injection needle assembly as defined in claim 1, wherein the predefined wall thickness $t_{1,lim}$ is selected between 0.12 mm and 0.3 mm.

12. The injection needle assembly as defined in claim 1, wherein the shaft section comprises one or more reinforcing ribs having a wall thickness greater than 1.5 times $t_{1,lim}$.

13. An injection device comprising the injection needle assembly as defined in claim 1, the injection device further comprising a needle shield with a needle opening, the needle shield and the injection needle assembly being arranged axially slidably relative to each other for causing the needle cannula to penetrate the needle cover and protrude through the needle opening of the needle shield.

14. The injection device as defined in claim 13, wherein the injection device is configured as an auto-injector that is triggerable by relative movement between the needle shield and the injection needle assembly and wherein the needle shield is configured to act on the needle cover for causing the needle cover to be penetrated by the needle cannula.

15. The injection device as defined in claim 13, wherein radially outwards facing surfaces of the shaft section and the bulb section of the needle cover is radially spaced apart from the needle shield at least as the needle shield and the injection needle assembly slides relative to each other for causing the needle cannula to penetrate the needle cover.

16. The injection needle assembly as defined in claim 1, wherein the $t_2$ defines the wall thickness greater than 0.5 mm.

17. The injection needle assembly as defined in claim 1, wherein the $t_2$ defines the wall thickness greater than 0.6 mm.

18. The injection needle assembly as defined in claim 1, wherein the $t_2$ defines the wall thickness greater than 0.7 mm.

19. The injection needle assembly as defined in claim 1, wherein the annular region of the reduced wall thickness between 0.18 mm to 0.25 mm separates the first annular bulb region and the second annular bulb region.

20. The injection needle assembly as defined in claim 1, wherein at least a portion of said needle cover is polished.

21. The injection needle assembly as defined in claim 1, wherein at least a portion of said needle cover is spark eroded with an A3 polishing.

22. The injection needle assembly as defined in claim 1, wherein the needle cover in the first configuration, comprises a radially inwards facing surface with a diameter within the range 2.2 mm to 3.0 mm.

23. The injection needle assembly as defined in claim 1, wherein the needle cover in the first configuration, comprises a radially inwards facing surface with a diameter within the range 2.4 mm to 2.6 mm.

24. The injection needle assembly as defined in claim 1, wherein the predefined wall thickness $t_{1,lim}$ is selected between 0.15 mm and 0.25 mm.

25. The injection needle assembly as defined in claim 1, wherein the predefined wall thickness $t_{1,lim}$ is selected between 0.17 mm and 0.20 mm.

26. The injection needle assembly as defined in claim 1, wherein the wall thickness $t_3$ is selected between 0.23 mm to 0.28 mm.

\* \* \* \* \*